(12) United States Patent
Peligrad

(10) Patent No.: US 8,891,842 B2
(45) Date of Patent: Nov. 18, 2014

(54) FUNCTIONAL IMAGING

(75) Inventor: Dragos-Nicolae Peligrad, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 259 days.

(21) Appl. No.: 13/575,308

(22) PCT Filed: Jan. 7, 2011

(86) PCT No.: PCT/IB2011/050068
§ 371 (c)(1),
(2), (4) Date: Jul. 26, 2012

(87) PCT Pub. No.: WO2011/095898
PCT Pub. Date: Aug. 11, 2011

(65) Prior Publication Data
US 2012/0314925 A1 Dec. 13, 2012

Related U.S. Application Data

(60) Provisional application No. 61/300,491, filed on Feb. 2, 2010.

(51) Int. Cl.
| | |
|---|---|
| *G06K 9/00* | (2006.01) |
| *A61B 6/00* | (2006.01) |
| *A61B 6/03* | (2006.01) |
| *A61B 8/00* | (2006.01) |
| *G06T 7/00* | (2006.01) |
| *A61B 8/08* | (2006.01) |

(52) U.S. Cl.
CPC ............... *A61B 6/481* (2013.01); *A61B 6/037* (2013.01); *A61B 6/469* (2013.01); *A61B 6/5247* (2013.01); *A61B 8/4416* (2013.01); *G06T 7/0016* (2013.01); *A61B 8/481* (2013.01); *G06T 2207/10084* (2013.01); *G06T 2207/30096* (2013.01)
USPC .......................................................... 382/128

(58) Field of Classification Search
USPC ................................................. 382/128–134
See application file for complete search history.

(56) References Cited

U.S. PATENT DOCUMENTS 7,175,829 B2    2/2007   Lauffer et al.
7,933,435 B2 *  4/2011   Hunter et al. .................. 382/128

(Continued)

FOREIGN PATENT DOCUMENTS

| WO | 2008155738 A2 | 12/2008 |
| WO | 2009126018 A1 | 10/2009 |
| WO | 2009146388 A1 | 12/2009 |

OTHER PUBLICATIONS

Avril, N. E., et al.; Monitoring Response to treatment in patients utilizing PET; 2005; Radiol. Clin. North Am.; 43(1) abstract.

(Continued)

*Primary Examiner* — Alex Liew

(57) ABSTRACT

A method includes obtaining a first image of first contrast agent uptake in non tissue of interest of a patient. The first image is generated based on data from first data from a first imaging modality. The method further includes obtaining a second image of second contrast agent uptake in tissue of interest and the non tissue of interest of the patient. The second image is generated based on second data from a second different imaging modality. The method further includes generating a first image mask based on the first image and generating a first feature image based on the second image and the first image mask. The method further includes displaying at least the first feature image.

26 Claims, 5 Drawing Sheets

(56) References Cited

U.S. PATENT DOCUMENTS

| | | | |
|---|---|---|---|
| 2003/0233039 A1* | 12/2003 | Shao et al. | 600/407 |
| 2004/0153128 A1* | 8/2004 | Suresh et al. | 607/14 |
| 2007/0014452 A1* | 1/2007 | Suresh et al. | 382/128 |
| 2007/0092864 A1* | 4/2007 | Reinhardt et al. | 435/4 |
| 2007/0100226 A1* | 5/2007 | Yankelevitz et al. | 600/407 |
| 2008/0144895 A1* | 6/2008 | Hunter et al. | 382/128 |
| 2008/0146914 A1* | 6/2008 | Polzin et al. | 600/420 |
| 2009/0264753 A1 | 10/2009 | von Schulthess et al. | |
| 2009/0316970 A1* | 12/2009 | Kemper et al. | 382/131 |
| 2010/0172562 A1* | 7/2010 | Satoh et al. | 382/131 |

OTHER PUBLICATIONS

Barentsz, J. O., et al.; Use of ultrasmall superparamagnetic iron oxide in lymph node MR imaging in prostate cancer patients; 2007; European Journal of Radiology; 63:369-372.

Harisinghani, M. G., et al.; MR Lymphangiography: Imaging Strategies to Optimize the Imaging of Lymph Nodes with Ferumoxtran-10; 2004; RadioGraphics; 24:867-878.

Kawahara, I., et al.; Potential of Magnetic Resonance Plaque Imaging Using Superparamagnetic Particles of Iron Oxide for the Detection of Carotid Plaque; 2008; Neurol. Med. Chir (Tokyo); 48:157-162.

Macmanus, M. P., et al.; Overview of early response assessment in lymphoma with FDG-PET; 2007; Cancer Imaging; 7:10-18.

Ng, M.; Use of FDG-PET to monitor response to chemotherapy and radiotherapy in patients with lymphomas; 2006; Eur J Nucl Med Mol Imaging; 33 Suppl 1:abstract.

Peng, X-H, et al.; Targeted magnetic iron oxide nanoparticles for tumor imaging and therapy; 2008; International Journal of Nanomedicine; 3(3)311-321.

Pfluger, T., et al.; Multimodal Imaging Using PET and MRI; 2006; in "Pediatric PET Imaging"; Chapter 27; pp. 485-501.

Taupitz, M., et al.; Superparamagnetic Iron Oxide Particles: Current State and Future Development; 2003; Fortschr Rontgenstr; 175:752-765.

Thorek, D. L. J., et al.; Superparamagnetic Iron Oxide Nanoparticle Probes for Molecular Imaging; 2006; Annls of Biomedical Engineering; 34:23-38.

Townsend, D. W.; Multimodality imaging of structure and function; 2008; Phys. Med. Biol.; 53(4):R1-R9.

Weber, W. A.; Use of PET for Monitoring Cancer Therapy and for Predicting Outcome; 2005; Journal of Nuclear Medicine; 46(6)983-995.

Weber, W. A.; PET for response assessment in oncology: radiotherapy and chemotherapy; 2005; The British Institute of Radiology; PET scanning in radiotherapy; Suppl. 28:42-49.

Weber, W. A., et al.; Monitoring chemotherapy and radiotherapy of solid tumors; 2006; European Journal of Nuclear Medicine and Molecular Imaging; 33(13)S27-S37.

* cited by examiner

FUNCTIONAL IMAGING

CROSS REFERENCE TO RELATED APPLICATIONS

This application claims the benefit of U.S. provisional application Ser. No. 61/300,491 filed Feb. 2, 2010, which is incorporated herein by reference.

The following generally relates to functional imaging and finds particular application with positron emission tomography (PET) and magnetic resonance (MR) imaging; however, it also amenable to other applications, including, but not limited to computed tomography (CT), ultrasounds (US), and/or other medical and non-medical imaging applications.

Functional positron emission tomography (PET) imaging has been used to determine information about cell metabolism and the cellular transport processes. By way of example, FDG PET has been used to image dynamic metabolic tracer (FDG, a glucose analog) uptake in tissue with high glucose metabolism, such as tumor cells, and provide quantitative information about the tissue. One such quantitative measure is the standardized uptake value (SUV), which has been used to monitor the progress of tumor during (chemo/radio) therapy. Generally, FDG uptake in a baseline scan (before therapy) is higher in tumor cells relative to FDG uptake in other cells and/or in the blood. During therapy, tumor cells are killed. Therefore, a reduction in FDG uptake during and shortly after therapy is usually interpreted as indicative of both fractional cell kill and regression of tumor volume, and is generally interpreted as a response to the therapy.

However, the quantitative measures of FDG uptake are limited because they measure the total activity or uptake in a region which may include tumor cells, inflamed cells (macrophages), and vascularization. As such, the quantitative measures include FDG uptake in the tumor cells, in the inflamed cells, and in the blood. Unfortunately, therapy treatment (e.g., radiation therapy) may induce inflammation in "normal" and/or necrotic non-tumor tissue in the region, which may increase the FDG uptake in the region. Thus, although the therapy treatment may kill tumor cells, which reduces the amount of FDG uptake in the region, the inflamed tissue and vascularization may increase FDG uptake in the region. In one instance, the increase in FDG uptake may be greater than the decrease in FDG uptake such that the total FDG uptake (tumor, macrophages and blood) after the therapy is higher than it was before the therapy, even though tumor cells were killed.

As a consequence, a before and after therapy differentiation based solely on the change in the magnitude of a FDG SUV measurement may lead to false-positive results, misdiagnosis of malignancies, etc. Additionally due to the inherent low spatial resolution of the PET detection system, the heterogeneity within a considered region generally may not be readily resolvable. Therefore, the blood volume fraction within a tumor, which is also affected by therapy and contributes to the overall signal, may be an additional source for a misdiagnosis of the therapy outcome.

Aspects of the present application address the above-referenced matters and others.

According to one aspect, a method includes obtaining a first image of first contrast agent uptake in non tissue of interest of a patient. The first image is generated based on first data from a first imaging modality. The method further includes obtaining a second image of second contrast agent uptake in tissue of interest and the non tissue of interest of the patient. The second image is generated based on second data from a second different imaging modality. The method further includes generating a first image mask based on the first image and generating a first feature image based on the second image and the first image mask. The method further includes displaying at least the first feature image In another aspect, an apparatus includes a mask generator that generates a first image mask based on a first image of first contrast agent uptake in non tissue of interest and a feature extractor that generates a feature image based on a second image of second contrast agent uptake in tissue of interest and the non tissue of interest patient and the first image mask.

In another aspect, a computer readable storage medium encoded with computer executable instructions, which, when executed by a processor of a computer, cause the computer to perform various acts. The acts include obtaining a quantified MR image of first contrast agent uptake in non tissue of interest of a patient, obtaining a quantified PET image of FDG uptake in tissue of interest and the non tissue of interest of the patient, generating an image mask based on the quantified MR image, and generating a feature image based on the quantified PET image and the image mask.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
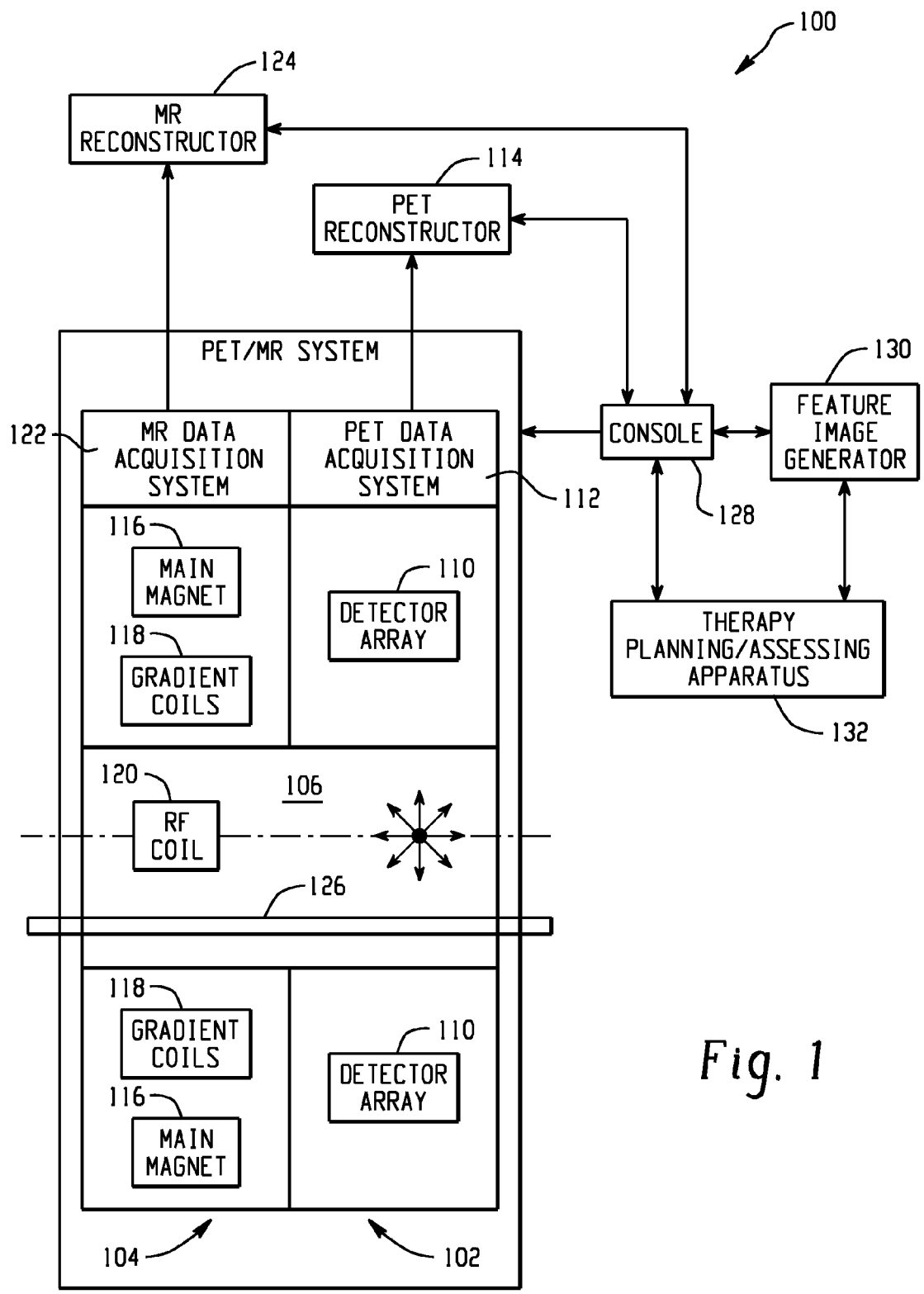
FIG. 1 illustrates an exemplary combination MR/PET imaging system in connection with a feature image generator.

FIG. 1 illustrates a single imaging system 100 that includes both a PET gantry portion 102 and a MR gantry portion 104, which share an examination region 106. The PET and MR gantry portions 102 and 104 can be used for both non-contrast enhanced studies and contrast enhanced studies. In another embodiment, the PET and MR gantry portions 102 and 104 are respectively part of separate PET and MR imaging systems. With such an embodiment, the PET gantry portion 102 can be part of a PET imaging system or a combined PET/computed tomography (PET/CT) imaging system.

The PET gantry portion 102 includes a gamma ray radiation sensitive detector array 110 disposed about the examination region 106. The detector array 110 includes one or more scintillation crystals and corresponding photosensors, such as photomultiplier tubes, photodiodes, etc. The crystals produce light when struck by a gamma ray, and the photosensors receive the light and generate electrical signals indicative thereof. A PET data acquisition system 112 processes the signals and generates PET data. In one instance, the PET data includes a list of annihilation events detected during data acquisition. The list generally includes, for each entry, information such as a time at which the event was detected, a position and orientation of the corresponding line-of-response (LOR), etc. Where the PET portion 102 is configured with time-of-flight (TOF) capabilities, an estimate of the position of the annihilation along the LOR is also included. A PET reconstructor 114 reconstructs the PET data and generates PET images.

The MR gantry portion 104 includes a main magnet 116, gradient (x, y, and z) coils 118, and a RF coil 120. The main magnet 116 (which can be a superconducting, resistive, permanent, or other type of magnet) produces a substantially homogeneous, temporally constant main magnetic field $B_0$ in the examination region 106. The gradient coils 118 generate time varying gradient magnetic fields along the x, y, and z-axes of the examination region 106. The illustrated RF coil 120 includes a transmit portion that produces radio frequency signals (at the Larmor frequency of nuclei of interest (e.g., hydrogen, etc.)) that excite the nuclei of interest in the examination region 106 and a receive portion that detects MR signals emitted by the excited nuclei. In other embodiments, the transmit portion and the receive portion of the RF coil 120 are located in separate RF coils. A MR data acquisition system 122 processes the MR signals, and a MR reconstructor 124 reconstructs the data and generates MR images.

A subject support 126 supports a subject such as a human or animal patient in the examination region 106. The support 126 is longitudinally movable in coordination with operation of the PET/MR system 100 so that the subject can be scanned at a plurality of longitudinal locations by one or both of the PET and MR gantry portions 102 and 104. An operator console 128, such as a computer, allows a user to operate the imaging system 100. The operator console 128 includes one or more processors for executing computer readable instructions encoded on computer readable storage medium. The console 128 also includes an output device such as a monitor or display and an input device such as a keyboard and/or a mouse.

A feature image generator 130 generates a feature image for tissue of interest (specific targeted tissue) based on MR and PET images. As described in greater detail below, this includes generating the feature image based on a functional PET image of PET contrast agent uptake in tissue of interest and tissue other than the tissue of interest (unspecific target tissue) (hereafter referred to also as non tissue of interest) and a contrast enhanced (CE) MR image of MR contrast agent uptake in the non tissue of interest, using the same region of interest (ROI) and volume(s) of interest (VOI(s)) for all of the images. In one instance, the CE MR image is used to create a mask that masks out the portions of the functional PET image corresponding to contrast agent uptake in the non tissue of interest, and the portions of the functional PET image corresponding to contrast agent uptake in the tissue of interest can then be extracted. The feature image can be variously used in connection with a therapy planning/assessing apparatus 132, which is used to plan a therapy, change a therapy plan, etc.

For example, for an oncology study a feature image generated before therapy treatment can be used to facilitate staging a tumor, planning (chemo, radio targeted, etc. therapy, ablation, etc.) treatment, etc. The feature image also allows for visualization of the tumor margin and thus can contribute to the improvement of tumor delineation procedures and definition of gross target volume (GTV) in radiotherapy planning. A feature image generated during or after can be used to facilitate differentiating between therapy induced inflammation and (neo)vascularisation and the viable tumor, and allows for extracting the residual tumor component, and, thus, facilitates assessing (e.g., for effectiveness), changing, terminating, etc. the therapy treatment, reducing side effects, reducing toxicity, reducing dose, etc. The during or after feature image can be used alone or in combination with a before therapy feature image, for example, for comparison, to generate a difference image, etc.

For cardiology studies, the feature image can be used to detect high risk or vulnerable plaques. By way of example, macrophages provide a sensitive and specific marker for atherosclerosis and inflammation within carotid plaques since the infiltration of macrophages are involved in plaque destabilization. The feature image, in this case, can be used to identify contrast uptake in the inflammation (macrophages) regions, which, due to the lower spatial resolution of the PET scanners, may be otherwise difficult to separate from the uptake in the blood. Generally, these inflammation regions are very near to the main blood vessel (e.g., the carotid artery) and thus it is beneficial to have a reliable procedure to separate the contrast agent uptake in the macrophages from the uptake in the blood. The separation of the uptake also facilitates quantifying SUV values for discriminating between macrophage-rich tissue and macrophage-poor tissue. As a result, the detection of vulnerable plaques with increased infiltration of macrophages may be improved prior to surgery and/or during follow-up.

Other applications are also contemplated herein.

It is to be appreciated that the illustrated feature image generator 130 is part of a computing system that includes one or more processors that execute computer readable instructions encoded in computer readable storage medium thereof. In another embodiment, the feature image generator 130 is part of or integrated with the console 128. In yet another embodiment, the feature image generator 130 is located separate from the system 100. In still another embodiment, the feature image generator 130 is a single or distributed system.

Figure 2:
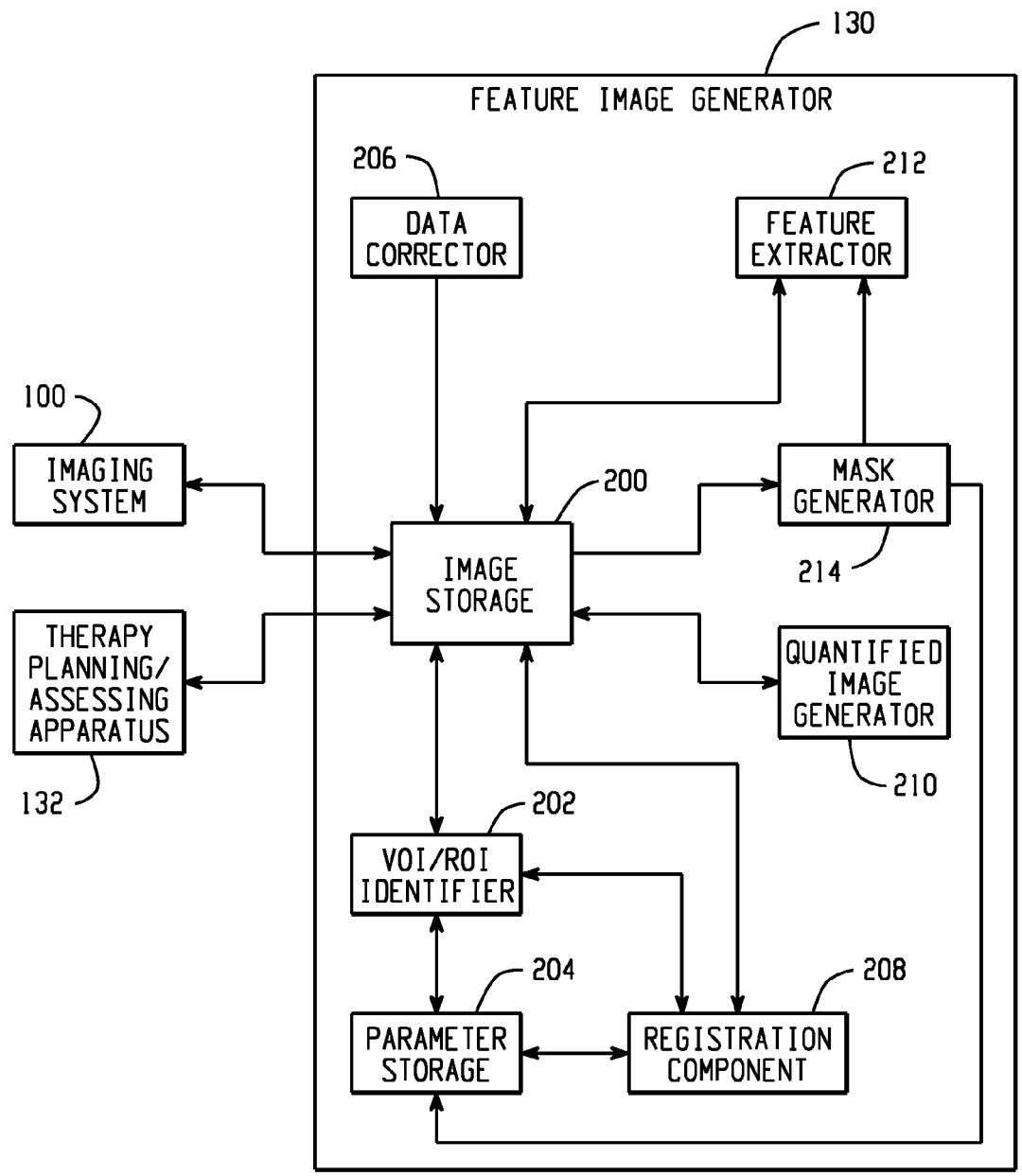
FIG. 2 illustrates an example feature image generator.

FIG. 2 illustrates a non-limiting example of the feature image generator 130 and is described in connection with a tumor application.

Image storage 200, such as memory, stores images including MR and PET images from the system 100, images generated by the feature image generator 130, and/or other images. This includes, but is not limited to, contrast enhanced images, non-contrast enhanced images, functional images, quantitative images, feature images, and/or other images. The illustrated image storage 200 is shown in communication with the system 100. However, in other embodiments, the image storage 200 is additionally or alternatively in communication with one or more other systems and/or memory that stores images generated from data from imaging systems like the imaging system 100.

A region of interest/volume of interest (ROI/VOI) identifier 202 can be used to identify or define one or more regions of interest (ROIs) and/or one or more volumes of interest (VOIs) within at least one region of interest ROI). By way of non-limiting example, the ROI/VOI identifier 202 can be used to identify a ROI around one or more tumor cells (with or without a margin) and to identify one or more VOIs for one or more of the tumor cells in the ROI.

Thus, a VOI represents a subset of an ROI. The ROI and/or VOIs can be manually, semi-automatically, or automatically identified based on various information such as user input, an anatomical model, a segmentation algorithm, stored parameters for one or more previously identified ROIs and/or VOIs, etc. With a comparative study, where previously stored parameters for ROIs and/or VOIs are available, the ROI/VOI identifier 202 can employ the previously stored parameters to determine the ROIs and/or VOIs, for example, so that the same or substantially the same ROIs and/or VOIs are compared.

Parameter storage 204 can be used to store one or more parameters used to define identified ROI and/or VOIs. When using previously stored parameters for ROIs and/or VOIs, the parameters stored in the parameter storage 204 can be used. The parameter storage 204 can also be used to store other parameter, extracted information, registration information, modality information, patient information, study information, and/or other information.

A data corrector 206 variously processes the image data. Suitable processing includes, but is not limited to, applying a local motion correction, a global motion correction, a partial volume correction, a data normalization, and/or other algorithms. Motion of a subject may be measured using a suitable motion monitor such as a respiratory, cardiac, or other physiological monitor. Motion may also be detected via an analysis of the projection space and/or the image space data. In another embodiment, the data corrector 206 is omitted.

A registration component 208 registers images. In the illustrated example, this includes registering before therapy PET and MR images, during or after therapy PET and MR images, before and during or after PET images, before and during or after MR images, etc. The registrations are based on the parameters used to identify the ROI and/or VOI(s) and may include registering the ROI and VOIs and/or other information in the images. Where CT images are additionally or alternatively available (e.g., when the system includes a combined PET/CT scanner), the registration component 208 can also register PET with CT images and/or MR images with CT images. As noted herein, the registration component 208 may employ non-elastic (rigid) and/or elastic registration algorithms.

Note that the images can first be registered and then the ROIs and VOIs can be determined as described above based on the registered data.

A quantified image generator 210 generates quantified contrast images based on images in the image storage 200, including registered images. In one instance, the quantified-image image generator 210 includes a subtractor that subtracts a non-contrast enhanced image from a contrast enhanced image when generating a quantified contrast image. The quantified-image image generator 210 can generate quantified contrast images from PET, MR, US, and/or CT images.

A feature extractor 212 extracts a predetermined desired feature from the quantified contrast images. In one instance, the extracted feature is the part of an image that shows contrast uptake for particular tissue of interest, for example, tumor cells. As described in greater detail below, the feature extractor 212 may extracts the predetermined desired feature from quantified contrast images based on an image mask. By way of example, the feature extractor 212 may receive a functional PET image of PET contrast agent uptake in tissue of interest and in non tissue of interest and a CE MR image of MR contrast agent uptake in the non tissue of interest. A mask generator 214 can make a contrast MR mask of the non tissue of interest based on the CE MR image. The feature extractor 212 can use this mask to mask out portions of the PET image, such as portions showing contrast agent uptake in the non tissue of interest, leaving portions of the PET image showing contrast agent uptake in the tissue of interest. The mask can be stored in the parameter storage 204 or elsewhere.

Figure 3:
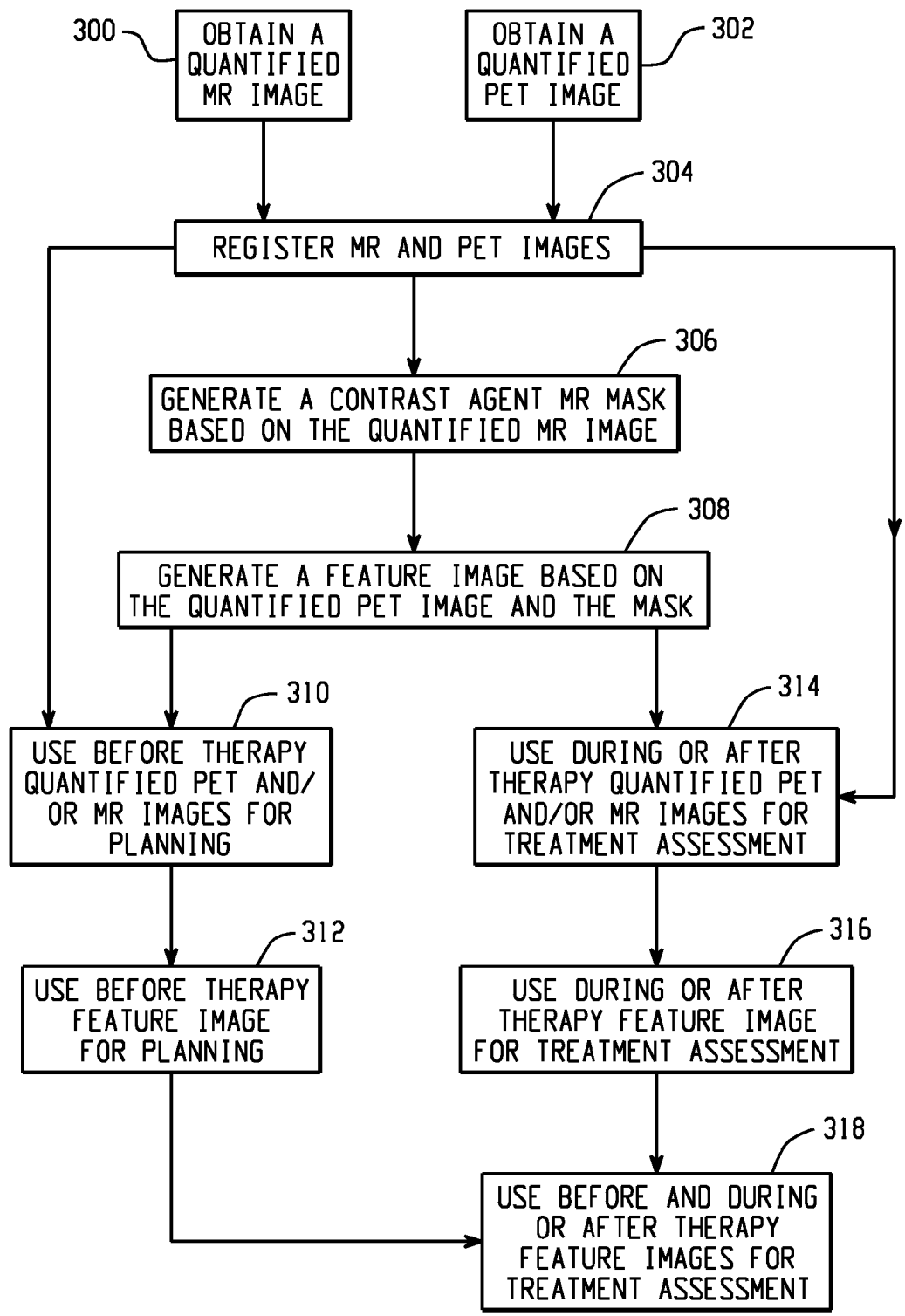
FIG. 3 illustrates a method employing the MR/PET imaging system of FIG. 1 and the feature image generator of FIG. 2 for a functional imaging study.
Figure 4:
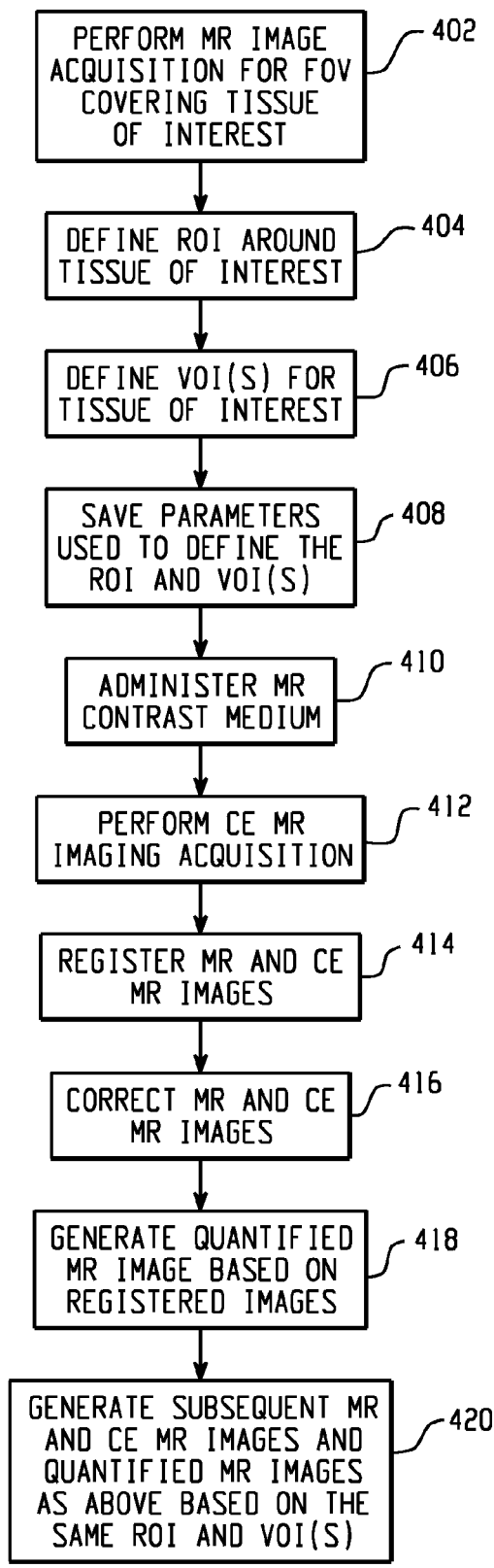
FIG. 4 illustrates a method for generating a quantified MR image used in the method of FIG. 3.
Figure 5:
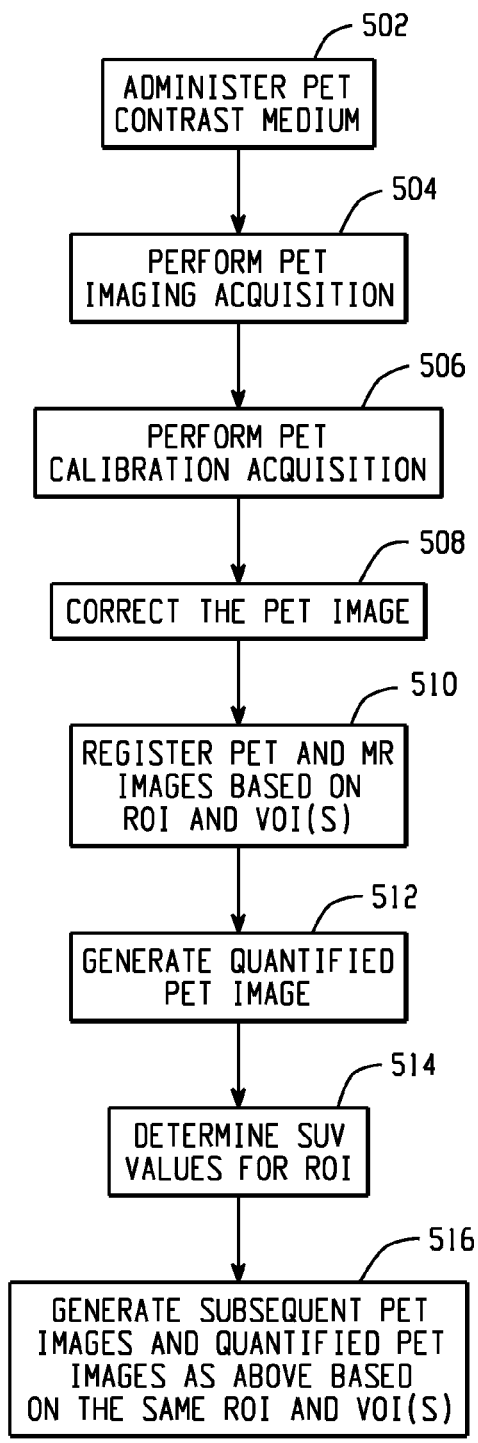
FIG. 5 illustrates a method for generating a quantified PET image used in the method of FIG. 3.

FIGS. 3, 4, and 5 describe a method for employing the system 100 for an oncology based study. It is to be appreciated that the ordering of the acts is non-limiting and one or more of the acts may occur in a different order. In addition, one or more of the acts may be omitted and/or one or more acts may be added.

At 300, a quantified MR image of first contrast agent uptake for an ROI and one or more VOIs in the ROI is obtained. In this example, the first contrast agent is an agent that generally is not taken up in tissue of interest (e.g., tumor cells) and taken up in non tissue of interest (e.g., non-tumor tissue, such as macrophages, blood, etc.) in the ROI. The quantified MR image can be generated as described below in FIG. 4.

At 302, a quantified PET image of second contrast agent uptake for the same ROI and the same one or more VOI is obtained. In this example, the second contrast agent is an agent that generally is taken up in tissue of interest (e.g., tumor cells) and non tissue of interest (e.g., non-tumor tissue) in the ROI. The quantified PET image can be generated as described below in FIG. 5.

Acts 300-302 can be performed before and during or after (chemo, radiation, targeted, etc.) therapy treatment.

At 304, the resulting images are registered based on the same ROI and VOIs.

At 306, a contrast agent MR image mask is generated based on the quantified MR image for at least the during or after therapy quantified MR image and optionally for the before therapy quantified MR image. The masks correspond to the non tissue of interest in the ROI.

At 308, a feature image of the PET contrast agent uptake in the tissue of interest is generated based on the quantified PET image and the contrast agent MR image mask. In one instance, this includes using the contrast agent MR image mask to mask the PET contrast agent uptake in the non tissue of interest in the quantified PET image and then extracting the PET contrast agent uptake in the tissue of interest in the masked quantified PET image to generate the feature image.

At 310, where a before therapy feature image is not generated, the before therapy quantified PET image and/or the before therapy quantified MR image can be used to stage a tumor, plan the therapy treatment, etc. At 312, where a before therapy feature image is generated, the before therapy feature image can additionally or alternatively be used.

At 314, where neither a before therapy or a during or after therapy feature image is generated, the individual quantified PET and MR images and/or a difference therebetween can be used to assess the therapy such as to monitor the progress of the therapy, to determine whether the therapy treatment plan should be changed, to facilitate changing one or more parameters of the therapy treatment plan, to determine whether to continue or terminate the therapy treatment plan, etc. At 316, where a before therapy feature image is not generated and a during or after therapy feature image is generated, the during or after therapy feature image can additionally or alternatively be used.

At 318, where both before therapy and during or after therapy feature images are generated, the before and during or after therapy quantified and feature images and/or difference images respectively therebetween can be used as noted above to assess the therapy.

Note that for the above acts, the same parameters used to identify the ROI and VOI(s) are used for all of the images. In one instance, this is achieved by registering the various images (using rigid and/or elastic registration algorithms) using the parameters employed to define the initial ROI and VOI(s) and storage in the parameter storage 204. Such registration may include registering MR and PET images both before and during or after therapy and registering MR and MR images and/or PET and PET images both before and during or after therapy. Where before and during or after CT scans are performed, such as the PET gantry portion is part of a combination PET/CT scanner and the MR gantry portion is part of a separate MR scanner, the PET images can be registered with the CT images and the CT images can be registered with the MR images based on the ROI and/or VOIs. The CT scan can be a lower dose or other CT scan.

Note that one or more of the images from the different modalities can also be fused to generate a fused image. Also note that one or more of images discussed above and/or one or more other images can be displayed, saved, and/or variously used, for example, to determined functional related information about the patient.

FIG. 4 illustrates a method for generating the quantified MR image discussed in act 302 of FIG. 3.

At 402, a standard (non-contrast enhanced) MR image acquisition for a field of view (FOV) covering tissue of interest (e.g., tumor cells) of a patient is performed.

At 404, a region of interest (ROI) is defined around the tissue of interest in the MR image data. The ROI may or may not include a margin around the tissue of interest.

At 406, one or more volumes of interest (VOI's) are defined for the tissue of interest (e.g., around individual tumor cells). In one instance, a VOI is defined such that the tissue within it is substantially homogeneous.

At 408, the parameters used to define the ROI and VOIs in the MR image data are stored in parameter storage 204.

At 410, a MR contrast medium is administered to the patient. A suitable contrast medium includes a contrast agent that generally is taken up by non tissue of interest (e.g., macrophages and/or vascularization), but not by the tissue of interest (e.g., the tumor cells).

A suitable contrast medium includes a contrast agent from the class of superparamagnetic MR contrast agents such as iron oxide particles. Such particles can range in size from tens of nanometers (nm) in diameter (USPIO, or Ultrasmall Super Paramagntic Iron Oxide), to hundreds of nanometers in diameter (SPIO), to larger than one (1) micron (μm) (MPIO). Generally, such an agent includes iron oxide (magnetite) cores, coated with dextran or siloxanes and encapsulated by a polymer. The surface can be further modified to facilitate internalization (penetration through cell membranes) or, by addition of antibodies, to facilitate a specific receptor mediated binding on specific target cell surfaces.

Generally, the (U)SPIO particles are sufficiently small to migrate through capillary pores in the intravascular extracellular space and to be internalized by both localized and migrating macrophages after lapse of a vascular circulation period. The localized macrophages can be found in organs such as bone marrow, lymph nodes, liver, and spleen. The migrating macrophages are mobilized by an inflammatory disease process in many other parts of the body. The (U)SPIO particles generally show only minimal leakage into inhomogeneous tumoral areas (mainly in the blood volume fraction within a tumor due to the increased vascular permeability and diffusion) and do not accumulate inside the viable tissue regions.

At 412, a contrast enhanced (CE) MR imaging acquisition is performed for the same field of view. An example of a suitable CE MR imaging acquisition includes a gated scan using $T_2^*$ or $T_1$-weighted detection.

At 414, the standard and CE MR images are registered using a rigid and/or elastic registration algorithm based on the initial ROI and/or VOIs (the ROI and VOIs saved in act 408 above).

At 416, the standard and CE MR images are optionally corrected for various artifacts due to local and/or global motion artifact, partial volume artifact, and/or other artifact.

At 418, a quantified MR image of the contrast uptake is generated based on the registered images. In one instance, this may include subtracting one of the MR images from the other of the MR images.

At 420, MR and CE MR images from subsequent MR imaging acquisitions using the above acts are also registered with the MR images based on the initial ROI and/or VOIs saved in act 408 above, and quantified MR images are generated therefrom. The MR images can be stored.

FIG. 5 illustrates a method for generating the quantified PET image discussed in act 304 of FIG. 3.

At 502, a PET contrast medium is administered to the patient. A suitable contrast medium includes an agent that is taken up by the tissue of interest, which, in this example, are tumor cells.

An example of such an agent includes a metabolic agent (or glucose analog) such as FDG ($^{18}$F-FDG, or fluorine-18-deoxyglucose) or other agent, which is taken up by high-glucose-using cells such as brain, kidney, tumor, etc. cells.

At 504, a FDG PET imaging acquisition is performed. A suitable PET imaging acquisition is a gated, whole body time-of-flight (TOF) contrast enhanced PET scan or other PET scan.

At 506, a calibration scan is performed with a calibration phantom. The calibration scan can be used to calibrate (or standardize) the PET image.

At 508, the PET image is optionally corrected for various artifacts due to local and/or global motion artifact, partial volume artifact, and/or other artifact.

At 510, the PET image is registered with the standard MR image (from act 402 of FIG. 4) using a rigid and/or elastic registration algorithm.

At 512, a quantified PET image of the contrast agent is generated.

At 514, a standard uptake value (SUV) is determined for the ROI in the PET image. In one instance, the SUV is determined based on the initial ROI and/or VOIs (the ROI and VOIs saved in act 408 of FIG. 4).

At 516, PET images from subsequent PET imaging acquisitions using the above acts are registered with previous PET images and subsequent MR images (from act 420 of FIG. 4) using a rigid and/or elastic registration algorithm and the initial ROI and/or VOIs (from act 408 of FIG. 4). The quantified PET image and the SUV are stored.

Figure 6:
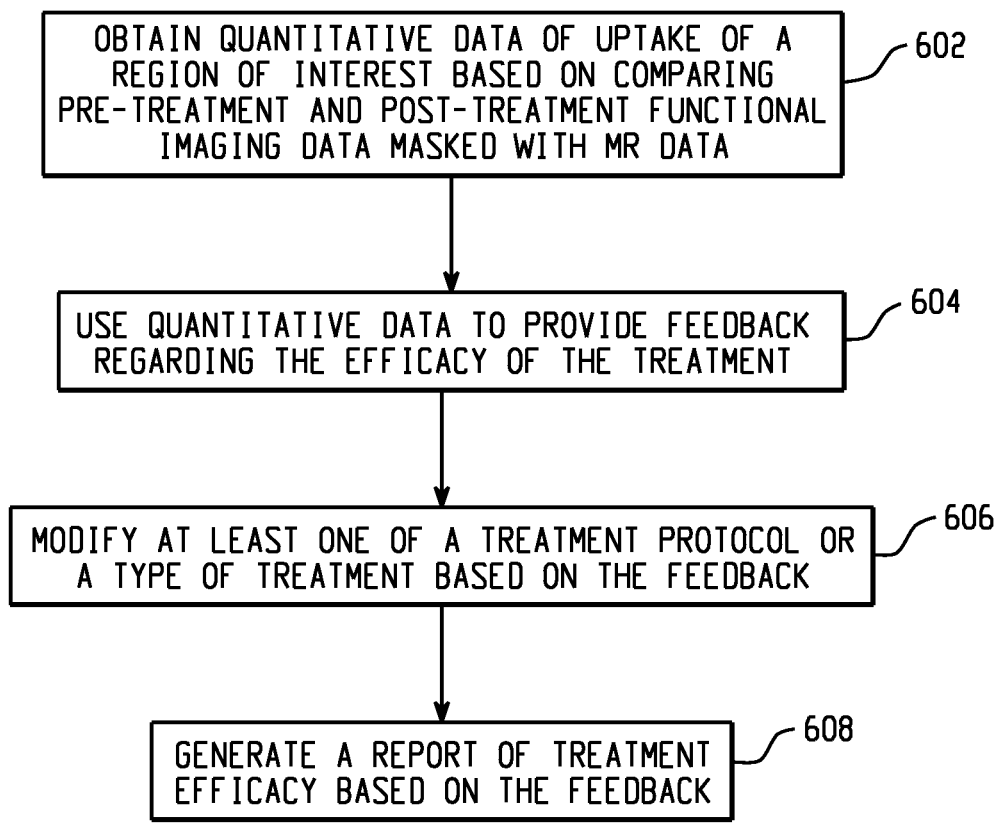
FIG. 6 illustrates a method of assessing treatment.

FIG. 6 illustrates a method of assessing treatment.

At 602, quantitative data of uptake of a region of interest based on comparing pre-treatment and post-treatment functional imaging data masked with MR data is obtained.

At 604, the quantitative data is used to provide feedback regarding the efficacy of the treatment.

At 606, at least one of a treatment protocol or a type of treatment is modified based on the feedback.

At 608, optionally, a report of treatment efficacy is generated based on the feedback.

Although embodiments herein have been described in connection with certain imaging modalities, it is to be understood that data from other imaging modalities may additionally or alternatively be used. By way of example, suitable imaging modalities include, but are not limited to, magnetic resonance (MR), positron emission tomography (PET), computed tomography (CT), single photon emission tomography (SPECT), radiography, ultrasound (US), and/or other imaging modalities.

The various techniques described herein may be implemented by way of a computer processor executing computer readable instructions encoded on a computer readable storage medium. Note that the medium need not be local to the processor; the instructions may be downloaded or otherwise accessed via a communication network such as the internet. The relevant computers may also be located remote from the imaging system, with the scan data transferred via a suitable network or other medium. The described techniques need not be performed concurrently with the data acquisition.

The invention has been described with reference to various embodiments. Modifications and alterations may occur to others upon reading the detailed description. It is intended that the invention be constructed as including all such modifications and alterations insofar as they come within the scope of the appended claims or the equivalents thereof.

What is claimed is:

1. A method, comprising:
obtaining a first image of first contrast agent uptake in non tissue of interest of a patient for a predetermined region of interest, wherein the first image is generated based on first data from a first imaging modality;
obtaining a second image of second contrast agent uptake in tissue of interest and the non tissue of interest of the patient for the same region of interest, wherein the second image is generated based on second data from a second different imaging modality;
generating a first image mask for the non tissue of interest in the region of interest based on the first image;
generating a first feature image by using the first image mask to mask the second contrast agent uptake in the non tissue of interest in the second image and extracting the second contrast agent uptake in the tissue of interest from the second image, wherein the first feature image includes the extracted second contrast agent Uptake in the tissue of interest in the second image; and
displaying at least the first feature image.

2. The method of claim 1, wherein the region of interest includes one or more volume of interests.

3. The method of claim 1, wherein the first and second images are pre-therapy images, and further comprising: planning a therapy treatment for the tissue of interest based on the first feature image.

4. The method of claim 1, wherein the first and second images are post-therapy images, and further comprising: assessing an affect of a therapy on the tissue of interest based on the first feature image.

5. The method of claim 1, further comprising:
obtaining a third image of third contrast agent uptake in the non tissue of interest, wherein the third image is generated based on third data from the first imaging modality;
obtaining a fourth image of fourth contrast agent uptake in the tissue of interest and the non tissue of interest, wherein the fourth image is generated based on fourth data from the second imaging modality;
generating a second image mask based on the third image; and
generating a second feature image based on the fourth image and the second image mask.

6. The method of claim 5, wherein the first and second images are pre-therapy images and the third and fourth images are post-therapy images, and further comprising: assessing a therapy treatment for the tissue of interest based at least on the first and second feature images.

7. The method of claim 6, further comprising:
generating a difference feature image based on the first and second feature images; and
assessing the therapy treatment based at least on the difference feature image.

8. The method of claim 1, wherein the first contrast agent is a superparamagnetic contrast agent.

9. The method of claim 1, wherein the second contrast agent is a metabolic contrast agent.

10. The method of claim 1, further comprising:
performing a standard MR acquisition for a field of view encompassing the tissue of interest and generating a MR image indicative thereof;
defining a region of interest around the tissue of interest and one or more volumes of interest for the tissue of interest;
administering the first contrast agent to the patient;
performing a contrast enhanced MR acquisition for the field of view and generating a contrast enhanced MR image indicative thereof;
registering the standard MR image and the contrast enhanced MR image based on the region of interest and the one or more volumes of interest; and
generating the first image based on the registered MR images.

11. The method of claim 10, further comprising: correcting at least one of the standard MR or the contrast enhance MR images for at least one of motion artifact or partial volume artifact.

12. The method of claim 10, further comprising:
administering the second contrast agent to the patient;
performing a functional PET acquisition for the field of view;
performing a calibration PET acquisition;
standardizing the functional PET acquisition data based on the calibration PET acquisition data;
registering the functional PET image with the standardized MR image based on the region of interest and the one or more volumes of interest; and
generating the second image based on the registered images.

13. The method of claim 12, further comprising: determining a standardized uptake value based on the second image.

14. The method of claim 10, further comprising: correcting the standardized functional PET image for at least one of motion artifact or partial volume artifact.

15. The method of claim 1, wherein the first image is a quantified MR image of the first contrast uptake.

16. The method of claim 1, wherein the second image is a quantified PET image of the second contrast uptake.

17. An apparatus, comprising:
a mask generator that generates a first image mask based on a first image of first contrast agent uptake in non tissue of interest; and
a feature extractor that generates a feature image based on a second image of second contrast agent uptake in tissue of interest, the non tissue of interest, and the first image mask by using the first image mask to mask third contrast agent uptake in non tissue of interest in the second image and extracting the second contrast agent uptake in the tissue of interest from the second image, wherein the feature image includes the extracted second contrast agent uptake in the tissue of interest in the second image.

18. The apparatus of claim 17, further comprising:
a quantified image generator that generates the first image based on first data from a first imaging modality and the second image based on second data from a second different imaging modality.

19. The apparatus of claim 17, wherein the feature image is indicates a response of the tissue of interest to therapy.

20. The apparatus of claim 17, wherein a therapy for the tissue of interest is planned based on the feature image.

21. The apparatus of claim 19, wherein the therapy is one of chemotherapy, radiation therapy, ablation, or targeted therapy.

22. The apparatus of claim 17, wherein the feature extractor generates a difference feature image based on a pre-therapy feature image and a post-therapy feature image.

23. The apparatus of claim 17, further comprising:
a registration component that registers the first and second images.

24. The apparatus of claim 23, wherein the registration component registers functional PET and contrast enhanced MR images.

25. The apparatus of claim 23, wherein the registration component registers at least one of a pre-therapy PET image and a post-therapy PET image or a pre-therapy MR image and a post-therapy MR image.

26. A computer readable storage medium encoded with computer executable instructions, which, when executed by a processor of a computer, cause the computer to perform the acts of:
obtaining a quantified MR image of first contrast agent uptake in non tissue of interest of a patient;
obtaining a quantified PET image of FDG uptake in tissue of interest and the non tissue of interest of the patient;
generating an image mask for the non tissue of interest based on the quantified MR image; and
generating a feature image based on the quantified PET image and the image mask by using the image mask to mask the uptake in the non tissue of interest in the PET image and extracting the uptake in the tissue of interest in the PET image, wherein the feature image includes the extracted uptake in the tissue of interest in the PET image.

* * * * *